(12) United States Patent
Kulach et al.

(10) Patent No.: US 7,467,060 B2
(45) Date of Patent: Dec. 16, 2008

(54) METHOD AND APPARATUS FOR ESTIMATING A MOTION PARAMETER

(75) Inventors: Christopher J. Kulach, Calgary (CA); James K. Rooney, Cochrane (CA); Paul R. MacDonald, Calgary (CA)

(73) Assignee: Garmin Ltd. (KY)

( * ) Notice: Subject to any disclaimer, the term of this patent is extended or adjusted under 35 U.S.C. 154(b) by 0 days.

(21) Appl. No.: 11/681,032

(22) Filed: Mar. 1, 2007

(65) Prior Publication Data

US 2007/0208544 A1  Sep. 6, 2007

Related U.S. Application Data

(60) Provisional application No. 60/778,793, filed on Mar. 3, 2006.

(51) Int. Cl.
*G04F 10/00* (2006.01)

(52) U.S. Cl. .................. 702/141; 702/160; 702/182; 702/176; 73/490; 73/514.01

(58) Field of Classification Search .......... 702/176, 702/141, 160, 182; 364/410, 561, 564; 73/490, 73/514.01
See application file for complete search history.

(56) References Cited

U.S. PATENT DOCUMENTS

| | | | | |
|---|---|---|---|---|
| 4,144,568 A | 3/1979 | Hiller et al. | ................... | 364/410 |
| 4,578,769 A | 3/1986 | Frederick | ................... | 364/565 |
| 4,703,445 A | 10/1987 | Dassler | ................... | 364/561 |
| 4,736,312 A | 4/1988 | Dassler et al. | ................... | 364/561 |
| 4,763,287 A | 8/1988 | Gerhaeuser et al. | ................... | 364/561 |
| 4,821,218 A | 4/1989 | Pötsch | ................... | 364/566 |
| 5,605,336 A | 2/1997 | Gaoiran et al. | ................... | 273/445 |
| 5,636,146 A * | 6/1997 | Flentov et al. | ................... | 702/176 |
| 5,724,265 A | 3/1998 | Hutchings | ................... | 364/565 |
| 5,925,001 A | 7/1999 | Hoyt et al. | ................... | 600/595 |
| 5,955,667 A | 9/1999 | Fyfe | ................... | 73/490 |
| 5,976,083 A * | 11/1999 | Richardson et al. | ......... | 600/300 |
| 6,018,705 A | 1/2000 | Gaudet et al. | ............... | 702/176 |
| 6,052,654 A | 4/2000 | Gaudet et al. | ............... | 702/160 |
| 6,135,951 A | 10/2000 | Richardson et al. | ......... | 600/300 |
| 6,145,389 A | 11/2000 | Ebeling et al. | ............. | 73/865.4 |
| 6,305,221 B1 | 10/2001 | Hutchings | ................... | 73/488 |

(Continued)

FOREIGN PATENT DOCUMENTS

DE  422373 A1  1/1994

(Continued)

OTHER PUBLICATIONS

Hayes, W.C. et al, Leg Motion Analysis During Gait by Multiaxial Accelerometry: Theoretical Foundations and Preliminary Validations, Journal of Biomechanical Engineering, vol. 105, pp. 283-289, Aug. 1983.

(Continued)

*Primary Examiner*—Bryan Bui
*Assistant Examiner*—Sujoy K Kundu
(74) *Attorney, Agent, or Firm*—Samuel M. Korte

(57) ABSTRACT

A method and apparatus for estimating a motion parameter corresponding to a subject element employs one or more accelerometers operable to measure accelerations and a processing system operable to generate a motion parameter metric utilizing the acceleration measurements and estimate the motion parameter using the motion parameter metric.

11 Claims, 7 Drawing Sheets

U.S. PATENT DOCUMENTS

| | | |
|---|---|---|
| 6,418,181 B1 | 7/2002 | Nissila ......................... 377/23 |
| 6,473,483 B2 | 10/2002 | Pyles ........................... 377/24 |
| 6,493,652 B1 | 12/2002 | Ohlenbusch et al. ........ 702/160 |
| 6,513,381 B2 | 2/2003 | Fyfe et al. ..................... 73/510 |
| 6,516,284 B2 | 2/2003 | Flentov et al. .............. 702/142 |
| 6,522,266 B1 | 2/2003 | Soehren et al. ............. 340/988 |
| 6,786,877 B2 | 9/2004 | Foxlin ........................ 600/587 |
| 6,813,582 B2 | 11/2004 | Levi et al. ................... 702/141 |
| 6,836,744 B1 | 12/2004 | Asphahani et al. ........... 702/141 |
| 6,876,947 B1 | 4/2005 | Darley et al. ................ 702/160 |
| 6,882,955 B1 | 4/2005 | Ohlenbusch et al. ........ 702/160 |
| 6,898,550 B1 | 5/2005 | Blackadar et al. ........... 702/182 |
| 6,958,045 B2 | 10/2005 | Takiguchi et al. ........... 600/595 |
| 7,054,784 B2 | 5/2006 | Flentov et al. .............. 702/149 |
| 7,152,286 B2 | 12/2006 | Rooney et al. ............. 24/712.6 |
| 7,200,517 B2 | 4/2007 | Darley et al. ................ 702/160 |
| 2004/0228503 A1 | 11/2004 | Cutler ........................ 382/103 |
| 2006/0020421 A1 | 1/2006 | Darley et al. ................ 702/182 |

FOREIGN PATENT DOCUMENTS

| | | |
|---|---|---|
| DE | 4222373 A1 | 1/1994 |
| GB | 2137363 A | 10/1984 |
| WO | WO99/44016 | 9/1999 |

OTHER PUBLICATIONS

Meijer, Gerwin A. L. et al, Methods to Assess Physical Activity with Special Reference to Motion Sensors and Accelerometers, IEEE Transactions on Biomedical Engineering, vol. 38, No. 3, pp. 221-229, Mar. 1991.

Notification of Transmittal of the International Search Report and the Written Opinion of the International Searching Authority or the Declaration, dated Mar. 14, 2008 from PCT/IB2007/002987, filed Mar. 2, 2007.

* cited by examiner

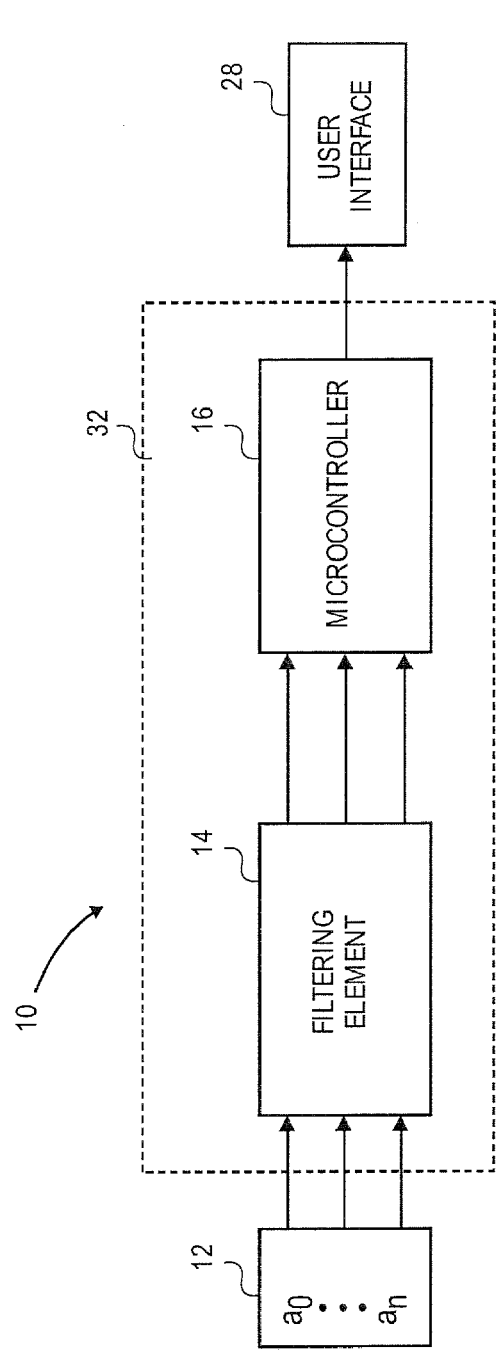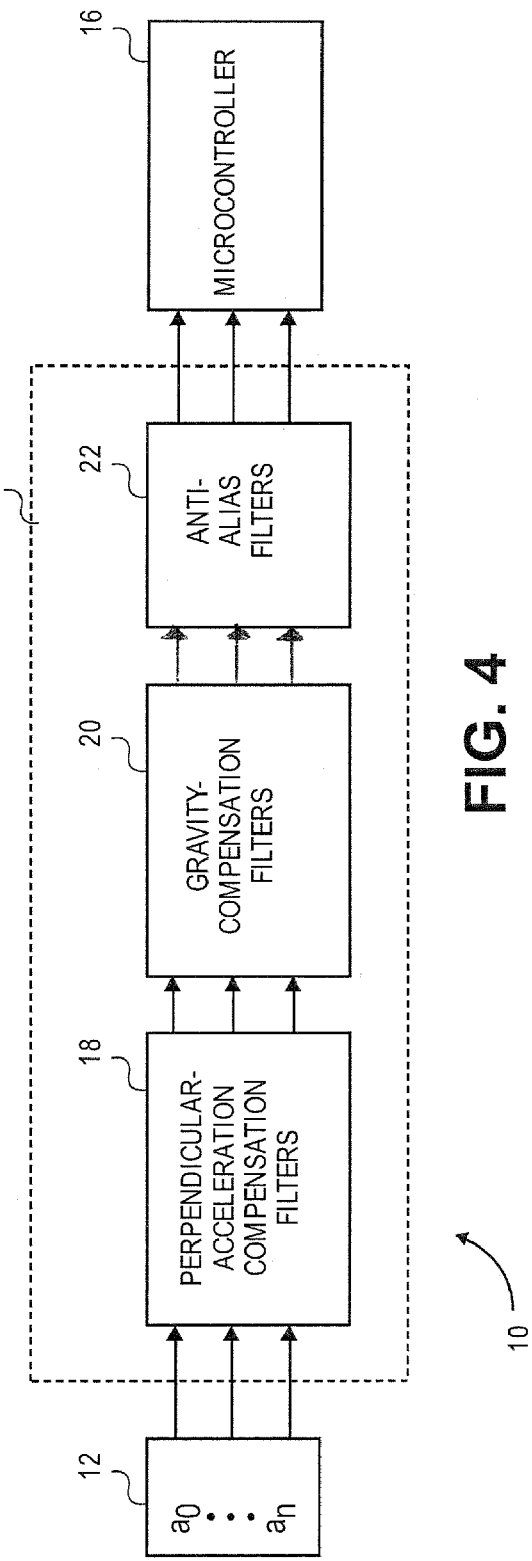

ary embodiments of the present invention provide
METHOD AND APPARATUS FOR ESTIMATING A MOTION PARAMETER

RELATED APPLICATIONS

The present application claims the benefit of U.S. Provisional Application No. 60/778,793, entitled "METHOD AND SYSTEM FOR QUICK DISTANCE MEASUREMENT," filed Mar. 3, 2006, which is herein incorporated by reference in its entirety.

BACKGROUND

1. Field

Embodiments of the present invention relate to methods and apparatuses for estimating motion parameters. More particularly, various embodiments of the invention provide methods and apparatuses operable to estimate a motion parameter utilizing one or more acceleration measurements.

2. Description of the Related Art

Motion parameters, such as acceleration, average velocity, stride distance, total distance, gait efficiency, and the like, may be utilized in the training and evaluation of athletes and animals, the rehabilitation of the injured and disabled, and in various recreational activities. Unfortunately, motion parameters acquired using commonly-available pedometers are often inaccurate due to stride lengths and other sensed attributes that vary while users move or exercise. Further, methods for compensating for changes in stride lengths often rely upon expensive, complex, and/or bulky equipment.

SUMMARY

The present invention is directed to methods and apparatuses operable to estimate a motion parameter utilizing one or more acceleration measurements. In various embodiments the present invention provides an apparatus including one or more accelerometers and a processing system. The one or more accelerometers are operable to measure accelerations and the processing system is operable to generate a motion parameter metric utilizing the acceleration measurements and estimate the motion parameter using the motion parameter metric. The motion parameter may be estimated for each of a user's strides to accurately reflect user performance.

It is to be understood that both the foregoing general description and the following detailed description are exemplary and explanatory only and are not necessarily restrictive of the invention claimed. The accompanying drawings, which are incorporated in and constitute a part of the specification, illustrate embodiments of the invention and together with the general description, serve to explain the principles of the invention.

BRIEF DESCRIPTION OF THE DRAWING FIGURES

Various embodiments of the present invention are described in detail below with reference to the attached drawing figures, wherein:

FIG. 3 is a block diagram illustrating some of the components operable to be utilized by various embodiments of the present invention;

FIG. 4 is a block diagram illustrating some of the components of FIG. 3 in more detail;

Figure 1:
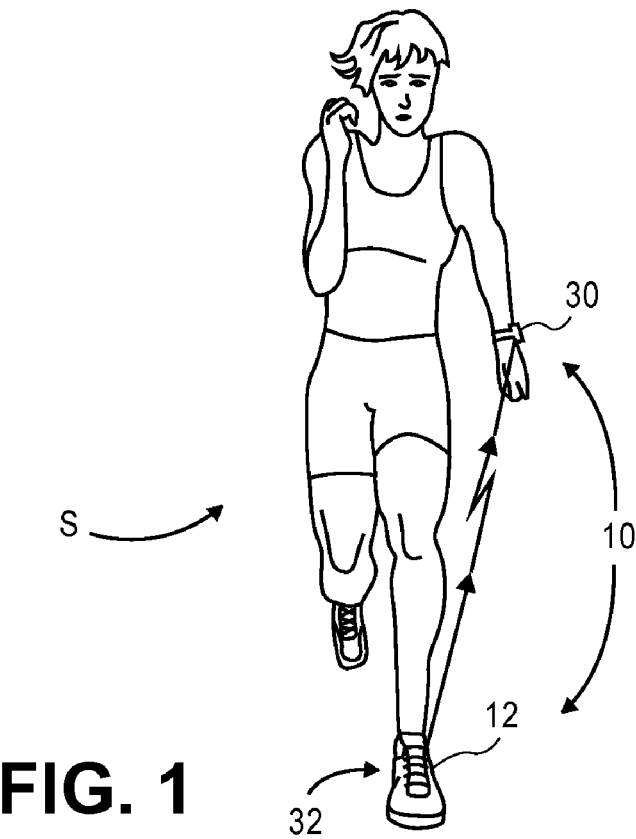
FIG. 1 is a schematic diagram illustrating a user employing a sensor unit and a user interface unit configured in accordance with various embodiments of the present invention.

The drawing figures do not limit the present invention to the specific embodiments disclosed and described herein. The drawings are not necessarily to scale, emphasis instead being placed upon clearly illustrating various embodiments of the invention.

DETAILED DESCRIPTION

The following detailed description of various embodiments of the invention references the accompanying drawings which illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Various embodiments of the present invention provide an apparatus 10 operable to estimate a motion parameter based on one or more acceleration measurements. In particular, the apparatus 10 is operable to generate a motion parameter metric that may be used to estimate the motion parameter. The motion parameter metric may be generated utilizing one or more acceleration measurements and/or other data and information sensed or acquired by the apparatus 10.

In various embodiments, the apparatus 10 includes one or more accelerometers 12, a filtering element 14, and a processing system 16. The accelerometers 12, filtering element 14, and processing system 16 may be integrated together or form discrete elements that may be associated with each other. The processing system 16 is generally operable to generate the motion parameter metric and estimate the motion parameter using one or more acceleration measurements provided by the one or more accelerometers 12 and/or filtering element 14.

The one or more accelerometers 12 are each operable to measure an acceleration and generate an acceleration measurement corresponding to the measured acceleration. The acceleration measurement may be embodied as a signal operable to be utilized by the filtering element 14 and/or processing system 16. In some embodiments, one or more of the accelerometers 12 may be operable to output an analog signal corresponding to an acceleration measurement. For instance, each accelerometer 12 may output an analog voltage signal that is proportional to measured accelerations. In some embodiments, one or more of the accelerometers 12 may include the ADXL321 accelerometer manufactured by ANALOG DEVICES of Norwood, Mass. However, the one or more accelerometers 12 may include any digital and analog components operable to generate a signal corresponding to a measured acceleration. Thus, in some embodiments, one or more of the accelerometers 12 are operable to output a digital signal representing measured accelerations.

Figure 2:
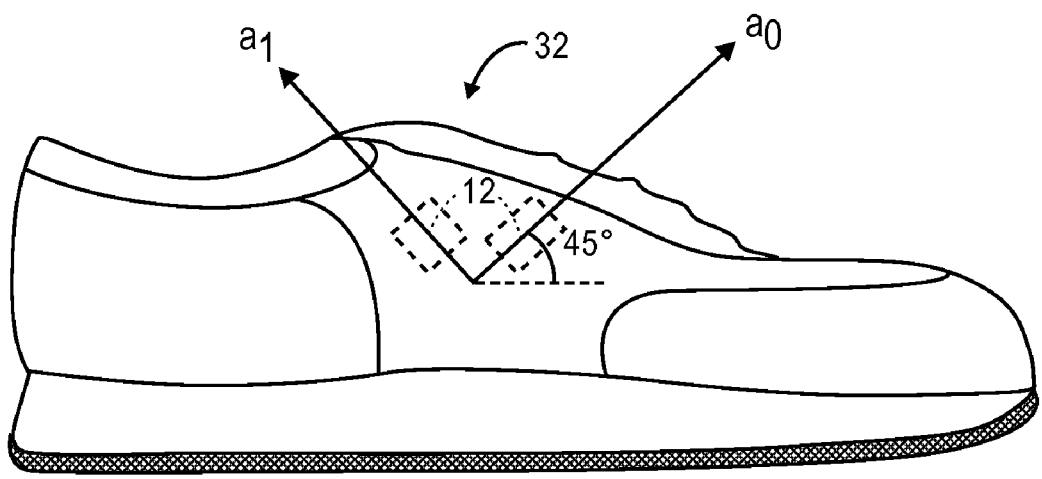
FIG. 2 is a schematic diagram illustrating an exemplary orientation of various sensors within or on a shoe.

The one or more accelerometers 12 are configured to couple with or attach to a subject element S that corresponds to the motion parameter sought to be estimated. In some embodiments, the subject element S may be a portion of a human, animal, or object. For example, as shown in FIGS. 1 and 2, one or more of the accelerometers 12 may be coupled with a runner's shoe to facilitate accurate estimation of motion parameters corresponding to the runner. In other embodiments, one or more of the accelerometers 12 may be coupled with other portions of a human or animal, and/or with inanimate objects such as balls, rackets, clubs, watches, clothing, bats, skis, motor vehicles, wheels, bicycles, combinations thereof, and the like, to enable motion parameters to be estimated for any subject element S.

In various embodiments, as shown in FIG. 2, the apparatus 10 may include two or more accelerometers 12 each operable to output a signal corresponding to a measured acceleration. In some embodiments, the apparatus 10 includes at least two accelerometers 12 adapted to measure accelerations in two directions separated by an angle greater than zero degrees and each provide a signal corresponding to the measured acceleration. Further, the apparatus 10 may include at least three accelerometers 12 adapted to measure accelerations in three directions each separated by an angle greater than zero degrees and each provide a signal corresponding to the measured acceleration. However, the apparatus 10 may include any number of accelerometers 12, including a single accelerometer 12, positioned in any configuration to provide acceleration measurements for use by the filtering element 14 and/or processing system 16.

In embodiments including at least two accelerometers 12 as shown in FIG. 2, a first one of the accelerometers 12 may measure acceleration along a first direction $a_0$ and a second one of the accelerometers 12 may measure acceleration along a second direction $a_1$. To facilitate the accurate estimation of the motion parameter, direction $a_0$ may be separated from direction $a_1$ by an angle of between about forty-five degrees and one-hundred thirty-five degrees. In some embodiments, direction $a_0$ may be substantially perpendicular to direction $a_1$ to facilitate the accurate estimation of motion parameters. In embodiments where the accelerometers 12 are coupled with a runner's shoe, directions $a_0$ and $a_1$ may be parallel to the sagittal plane of the subject element S.

In embodiments including at least three accelerometers 12, a first one of the accelerometers 12 may measure acceleration along a first direction $a_0$, a second one of the accelerometers 12 may measure acceleration along a second direction $a_1$, and a third one of the accelerometers 12 may measure acceleration along a third direction $a_2$. To facilitate the accurate estimation of motion parameters, the directions $a_0$, $a_1$, and $a_2$ may be separated from each other by angles of between about forty-five degrees and one-hundred thirty-five degrees. In some embodiments, each of the directions $a_0$, $a_1$, and $a_2$ may be substantially mutually perpendicular to each other to facilitate the accurate estimation of motion parameters.

In embodiments including only one of the accelerometers 12, the accelerometer 12 may be adapted to measure acceleration in a plane of motion substantially parallel to the sagittal plane of the subject element S. However, the accelerometer 12 may be positioned in any orientation to measure any acceleration component for use by the filtering element 14 and/or processing system 16. For instance, in embodiments where the accelerometer 12 is coupled with a runner's shoe, the accelerometer 12 may be configured to measure accelerations at an angle of about forty-five degrees from the plane of the shoe's sole.

The one or more of the accelerometers 12 may be operable to communicate with other elements of the apparatus 10, or elements external to the apparatus 10, through wired or wireless connections. Thus, the accelerometers 12 may be coupled with the filtering element 14 and/or processing system 16 through wires or the like. One or more of the accelerometers 12 may also be configured to wirelessly transmit data to other apparatus 10 elements and devices external to the apparatus 10. For instance, one or more the accelerometers 12 may be configured for wireless communication using various RF protocols such as Bluetooth, Zigbee, and/or any other wireless protocols.

The filtering element 14 is operable to couple with the one or more accelerometers 12 and filter acceleration measurements and/or signals corresponding to acceleration measurements. In some embodiments, the apparatus 10 does not include the filtering element 14 and the processing system 16 is operable to use unfiltered acceleration measurements and corresponding signals. In other embodiments, the filtering element 14 may be integral with one or more of the accelerometers 12, the processing system 16, or both the accelerometers 12 and the processing system 16. For example, a first portion of the filtering element 14 may be integral with one or more of the accelerometers 12 and a second portion of the filtering element 14 may be integral with the processing system 16. In other embodiments, the filtering element 14 may be discrete from both the accelerometers 12 and the processing system 16.

The filtering element 14 may include analog and digital components operable to filter and/or provide other pre-processing functionality to facilitate the estimation of motion parameters by the processing system 16. In various embodiments as shown in FIG. 4, the filtering element 14 is operable to filter signals provided by the one or more accelerometers 12, or signals derived therefrom, to attenuate perpendicular acceleration, to compensate for gravity, and/or to minimize aliasing. The filtering element 14 may include discrete components for performing each of these filtering functions or use the same components and hardware for these, and other, filtering functions.

The filtering element 14 may include any analog and digital components for filtering signals and measurements, including passive and active electronic components, processors, controllers, programmable logic devices, digital signal processing elements, combinations thereof, and the like. In some embodiments, the filtering element 14 may include a digital microcontroller, such as the MSP430F149 microcontroller manufactured by TEXAS INSTRUMENTS to provide various static and/or adaptive filters. The filtering element 14 may also include an analog-to-digital converter to convert analog signals provided by the one or more accelerometers 12 to digitize signals for use by the processing system 16. The filtering element 14 may also include conventional pre-sampling filters.

The perpendicular acceleration operable to be generally attenuated by the filtering element 14 corresponds to acceleration that is generally perpendicular to the direction of movement of the subject element S. For example, in embodiments where the subject element S is a human runner, the perpendicular acceleration generally corresponds to acceleration that is perpendicular to the average torso direction of the runner. In some embodiments, the filtering element 14 includes a low-pass filter 18 operable to attenuate components of the signals corresponding to measured accelerations that represent motion generally perpendicular to the direction of movement of the subject element S.

In some embodiments, the low-pass filter 18 may be an adaptive filter operable to employ static and/or varying cut-off frequencies between about 0.5 Hz and 10 Hz. In some embodiments where parameters corresponding to human strides are estimated, the low-pass filter 18 may employ cut-off frequencies between about 1 Hz and 3 Hz. The filtering element 14 may acquire the cut-off frequency from the processing system 16 based on computations performed by the processing system 16 corresponding to the particular stride frequency of the subject element S. The low-pass filter 18 may additionally or alternatively be adapted to employ a cut-off frequency corresponding to a gait type identified by the processing system 16.

In other embodiments, the cut-off frequency for the low-pass filter 18 may be a static value based upon the typical stride frequency of a running or walking human. For instance, the cut-off frequency may correspond to a frequency between one and two times the typical stride frequency of a running and/or walking human, such as a static frequency between 1 Hz and 3 Hz. Specifically, in some embodiments, the cut-off frequency may be about 1.45 Hz for walking humans and about 2.1 Hz for jogging humans.

The gravity compensation provided by the filtering element 14 generally compensates for the constant acceleration provided by gravity that may be sensed by one or more of the accelerometers 12. In some embodiments, the filtering element 14 includes a high-pass filter 20 operable to filter or attenuate components of signals corresponding to measured accelerations below a given cut-off frequency. The cut-off frequency of the high-pass filter 20 may correspond to a frequency approaching 0 Hz, such as 0.1 Hz, to adequately provide compensation for gravity-related acceleration.

The anti-aliasing provided by the filtering element 14 generally reduces or prevents aliasing caused by sampling of the signals provided by, or derived from, the one or more accelerometers 12. In some embodiments, the filtering element 14 includes a relatively wideband filter 22 designed to attenuate signal frequencies in excess of one-half of the sampling frequency used in any subsequent analog-to-digital conversions provided by the processing system 16 or other devices associated with the apparatus 10. In some embodiments, the filtering element 14 may provide other filtering components instead of, or in addition to, the wideband filter 22 to compensate for aliasing. For instance, the filtering element 14 may include one or more analog and/or digital filters to perform any combination of the various filtering functionality discussed herein. In some embodiments, a single filtering element may be utilized to perform each of the filtering functions discussed above such that separate or discrete filters are not necessarily employed for different filtering functions.

The processing system 16 is generally operable to couple with the one or more accelerometers 12 and/or the filtering element 14 to generate the motion parameter metric using one or more measured accelerations and estimate the motion parameter based on the generated motion parameter metric. The processing system 16 may include various analog and digital components operable to perform the various functions discussed herein. In some embodiments, the processing system 16 may include a microprocessor, a microcontroller, a programmable logic device, digital and analog logic devices, computing elements such as personal computers, servers, portable computing devices, combinations thereof, and the like.

To facilitate the generation of the motion parameter metric and estimation of the motion parameter, the processing system 16, filtering element 14, accelerometers 12, and/or other portions of the apparatus 10 may limit the dynamic range of acceleration measurements used to generate the motion parameter metric. For example, acceleration measurements outside a specified dynamic range, such as plus or minus 8 g, may be saturated at the dynamic range limits to further limit the effects of perpendicular acceleration. The dynamic range may be varied by the processing system 16 based on the particular motion parameter being estimated or according to other sensed or generated measurements.

The processing system 16 may also include, or be operable to couple with, a memory. The memory may include any computer-readable memory or combination of computer-readable memories operable to store data for use by the processing system 16. For instance, the memory may be operable to store acceleration data, motion parameter metric data, statistical data, motion parameter data, filtering data, configuration data, combinations thereof, and the like.

The processing system 16 may be discrete from the various accelerometers 12 and filtering element 14 discussed above. In other embodiments, the processing system 16 may be integral with other portions of the apparatus 10. For instance, the same microcontroller or microprocessor may be utilized to implement the filtering element 14 and the processing system 16.

In embodiments where the motion parameter to be estimated by the processing system 16 corresponds to a stride of a human or animal, the processing system 16 may be operable to determine the duration of the stride using measurements provided by the one or more accelerometers 12. For instance, based on various changes in accelerations measured by the one or more accelerometers 12, the processing system 16 may be able to determine the time at which a stride begins and ends, such as by determining when a runner's foot impacts the ground, when a runner's foot leaves the ground, when a runner's foot is stationary relative to the ground, combinations thereof, and the like. Thus, by analyzing various changes in measured accelerations, the processing system 16 may compute the stride duration and information corresponding thereto, such as stride frequency. The stride frequency may represent the number of strides per second or other indications of the rate of stride.

In some embodiments, the processing system 16 may provide the stride duration and/or stride frequency to the filtering element 14 for use in determining the various cut-off frequencies discussed above. Thus, the processing system 16 may dynamically determine the stride duration and stride frequency based on received acceleration measurements and the filtering element 14 may adapt to provide accurate filtration based on the particular performance of the subject element S. For example, the filtering element 14 may filter perpendicular acceleration based on the stride frequency calculated by the processing system 16 to facilitate the accurate estimation of the motion parameter.

The processing system 16 may additionally or alternatively be operable to determine and/or estimate the gait characteristics of the subject element S. By utilizing the accelerations measured by the accelerometers 12, the processing system 16 may determine if the subject element S, or animal or human corresponding to the subject element S, is walking, jogging, running, sprinting, idling, and the like. For instance, the processing system 16 may identify rapid and sustained accelerations to determine that a gait corresponds to running or sprinting. The processing system 16 may also determine, using the acquired accelerations, if the gait is efficient, high-impact, irregular, combinations thereof, and the like.

The motion parameter metric generated by the processing system 16 may be any metric that corresponds to the motion parameter to be estimated. In some embodiments where the motion parameter generally corresponds to stride speed, the motion parameter metric may correspond to the magnitude of the accelerations measured by the one or more accelerometers 12 and/or filtered by the filtering element 14. Acceleration magnitude may be defined as:

$$r^2(t) = a_0^2(t) + \ldots + a_n^2(t),$$

where r(t) is the magnitude of the resultant acceleration and $a_n(t)$ represents any number of measured and/or filtered accelerations. Any number of measured and/or filtered accelerations may be used to compute the acceleration magnitude, including a single acceleration.

In embodiments corresponding to stride speed that utilize acceleration magnitude, the processing system 16 may compute the motion parameter metric by integrating the acceleration magnitude. For instance, in various embodiments the motion parameter metric may be given by:

$$Q_0 = \frac{1}{T} \int_0^T \int_0^t r(\tau) d\tau dt,$$

where $Q_0$ is the motion parameter metric, T is the stride duration calculated by the processing system 16, and r(t) is the acceleration magnitude calculated by the processing system 16.

The motion parameter metric may additionally or alternatively be given by any of the following:

$$Q_1 = \frac{1}{T} \int_0^T \left( \sqrt{\int_0^t r^2(\tau) d\tau} \right) dt,$$

$$Q_2 = \frac{1}{T} \int_0^T \left( \sqrt{\int_0^t (r^2(\tau) - g^2) d\tau} \right) dt,$$

$$Q_3 = \frac{1}{T} \int_0^T \int_0^t \sqrt{(r^2(\tau) - g^2)} \, d\tau dt, \text{ and}$$

$$Q_4 = \frac{1}{T} \int_0^T \int_0^t (r(\tau) - g) d\tau dt,$$

where $Q_1$ through $Q_4$ represent various motion parameter metrics, T is the stride duration calculated by the processing system 16, r(t) is the acceleration magnitude calculated by the processing system 16, and g is the gravitational constant.

In embodiments using metrics $Q_1$ through $Q_4$, the subtraction of the gravitational constant g may be used to correct for gravity-related acceleration without the use of the high-pass filter 20 discussed above. However, any combination of metrics $Q_0$ through $Q_4$ may be employed in combination with the high-pass filter 20 to correct for gravity-related acceleration.

Any motion parameter metric may be utilized by the processing system 16 and embodiments of the present invention are not limited to the exemplary motion parameter metrics provided above. Further, the utilized metric may correspond to other factors acquired or calculated by the processing system 16. In some embodiments, the processing system 16 may select the metric based on the calculated gait of the subject element S or human or animal corresponding to the subject element S. For example, if the calculated gait is a walking gait, the processing system 16 may utilize the metric $Q_0$ while for other gaits the processing system 16 may utilize any one of metrics $Q_1$ through $Q_4$. Additionally, the processing system 16 may calculate a plurality of metrics, such as by using any combination of metrics $Q_0$ through $Q_4$ to facilitate estimation of the motion parameter.

The processing system 16 utilizes the one or more generated metrics to estimate the motion parameter. The estimation performed by the processing system 16 generally corresponds to a correlation between the motion parameter metric and motion parameter and is not necessarily a direct computation based on user kinematics. Consequently, the processing system 16 may estimate the motion parameter utilizing statistics and/or other empirical information even when a direct computation of the motion parameter is difficult or impossible to perform. The estimated motion parameter may correspond to stride speed, acceleration, velocity, stride distance, total distance, gait efficiency, power, energy, maximum impact, average calories consumed, maximum speed change, speed variability, combinations thereof, and the like. However, the estimated motion parameter may correspond to any parameter associated with the motion of the subject element S.

In some embodiments, the processing system 16 may estimate the motion parameter using the generated motion parameter metric and a statistical model. The statistical model may be a regression model selected from the group consisting of a linear regression model, a polynomial regression model, a multiple-regression model, a piecewise-linear regression model, combinations thereof, and the like.

Figure 11:
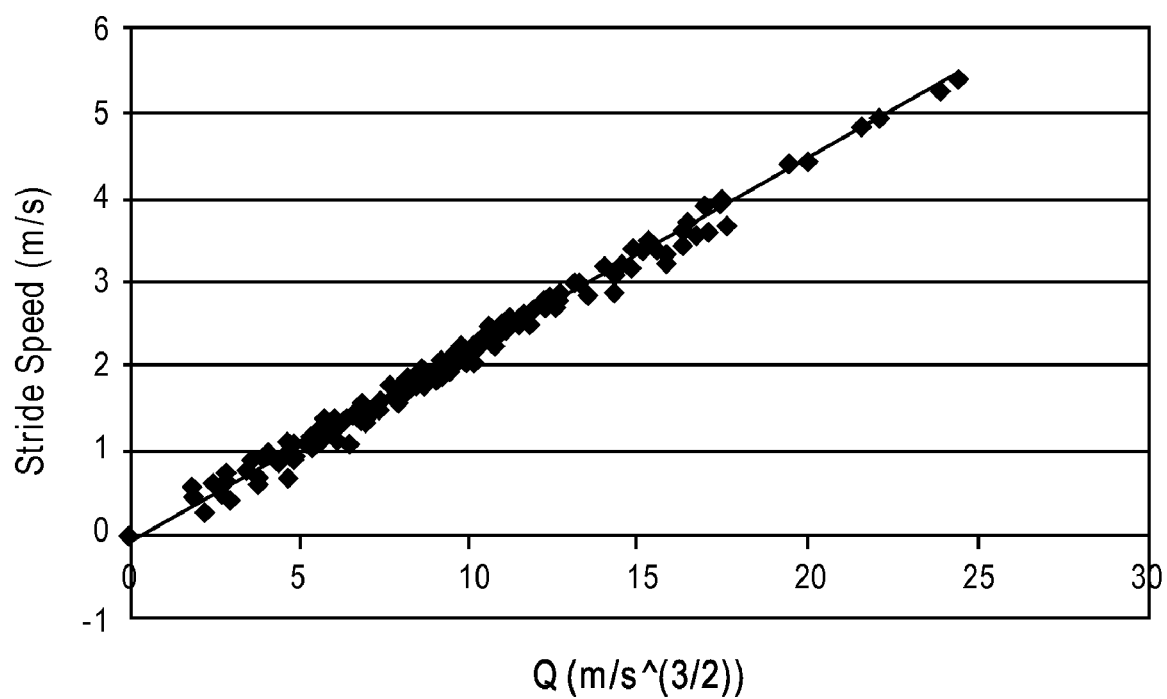
FIG. 11 is a chart showing an exemplary correlation between a motion parameter metric and stride speed.

For instance, the processing system 16 may correlate the generated motion parameter metric to stride speed as shown in the regression model of FIG. 11. In some embodiments, the processing system 16 may utilize a database, a look-up table, or other information stored within its memory to estimate the motion parameter using the motion parameter metric and the statistical model. For example, given a particular motion parameter metric, the processing system 16 may access the memory to acquire a corresponding motion parameter. Thus, in some embodiments the statistical model may comprise a database of information not limited to any particular regression model. As is discussed in more detail below, the processing system 16 may be operable to correct and/or adjust the statistical model using truth measurements and information provided from other sources.

The processing system 16 may also use a plurality of statistical models to estimate one or more motion parameters. In some embodiments, the processing system 16 may be configured to select which one or more of the statistical models may be used to estimate the motion parameter. For example, the processing system 16 may use information specific to the subject element S, such as age, gender, weight, height, configuration, shape, and the like, to select one or more of the statistical models. The processing system 16 may also select statistical models based on the configuration of the apparatus 10, such as the position of the one or more accelerometers 12 on the subject element S, the number and type of accelerometers 12 utilized, the number of acceleration measurements received, combinations thereof, and the like.

In various embodiments, the processing system 16 is operable to compute the motion parameter metric and/or estimate the motion parameter for each detected stride to facilitate the accurate analysis of movement. Thus, for every stride detected as discussed above, or for any combination of strides, the computing element may estimate the motion parameter. Further, in some embodiments, the processing system 16 may estimate the motion parameter using metrics corresponding to a plurality of strides. For example, the estimated motion parameter may correspond to a total or average stride speed resulting from several strides.

In some embodiments, each generated motion parameter metric and/or estimated motion parameter may be stored in the memory associated with the processing system 16, or in any other computer-readable memory, to allow later analysis by the processing system 16 or other devices associated therewith. The stored information may be time-correlated to facilitate analysis and compressed to reduce the required capacity of the memory.

The processing system 16 may additionally or alternatively utilize information acquired from sensors other than the one or more accelerometers 12. For instance, in some embodiments the processing system 16 may couple with a heart rate monitor, acquire heart rate information from the heart rate monitor, and generate the motion parameter metric and/or estimate the motion parameter using the heart rate information and/or acceleration measurements. Similarly, the processing system 16 may couple with other sensors to acquire non-acceleration kinematic variables such as velocity and/or environmental variables such as ambient temperature and altitude. For example, to acquire additional information, the processing system 16 may couple with, and/or include, radio-frequency transceivers, thermometers, altimeters, compasses, inclinometers, pressure sensors, blood pressure monitors, light sensors, atmospheric sensors, angular velocity sensors and other inertial sensors, microphones, computing devices such as personal computers, cellular phones, and personal digital assistances, other similarly configured apparatuses, combinations thereof, and the like.

In some embodiments, as shown in FIGS. 6 through 9, the apparatus 10 may be operable to receive information from at least one navigation device 24. The navigation device 24 may be adapted to provide geographic location information to the apparatus 10 and users of the apparatus 10. The navigation device 24 may include a GPS receiver much like those disclosed in U.S. Pat. No. 6,434,485, which is incorporated herein by specific reference. However, the navigation device 24 may use cellular or other positioning signals instead of, or in addition to, the GPS to facilitate determination of geographic locations. The navigation device 24 may be operable to generate navigation information such as the speed of the navigation device 24, the current and previous locations of the navigation device 24, the bearing and heading of the navigation device 24, the altitude of the navigation device 24, combinations thereof, and the like.

The processing system 16 may use the information received from the navigation device 24 to generate the motion parameter metric and/or to estimate the motion parameter. The processing system 16 may also use and present acquired navigation information independent of the metrics and estimated parameters. Additionally or alternatively, the processing system 16 may use the information acquired from the navigation device 24 to correct and/or adjust the statistical model. For instance, the processing system 16 may compare distances and speeds generated from accelerations provided by the one or more accelerometers 12 with distances and speeds provided by the navigation device 24 and correct the statistical model to enable distances and speeds generated from measured accelerations to be as accurate as those provided by the navigation device 24. Thus, the processing system 16 may be periodically coupled with the navigation device 24 to correct the statistical model to ensure that the apparatus 10 accurately estimates motion parameters even when not coupled with the navigation device 24.

The filtering element 14 and processing system 16 may additionally be operable to compensate for part-to-part manufacturing variability present in the one or more accelerometers 12, including characterization over temperature of zero-g bias point, sensitivity, cross-axis sensitivity, nonlinearity, output impedance, combinations thereof, and the like.

The apparatus 10 may also utilize information acquired from the navigation device 24 to form an error model operable to be used in combination with the statistical model to increase the accuracy of the estimated motion parameters. The error model can, for example, be linear as a function of speed. Furthermore, the error model can include dependence on other factors such as stride cadence, gait type, elevation change, gait efficiency or other gait characteristics.

Further, in some embodiments the apparatus 10 may utilize a user-calibration sequence where one or more motion parameters estimated by the apparatus 10 are compared to the true values of the parameters as supplied by a user. The user-calibration sequence may be used to further adjust the statistical model and/or motion parameter metrics to refine the accuracy of subsequent motion parameter estimations.

Figure 5:
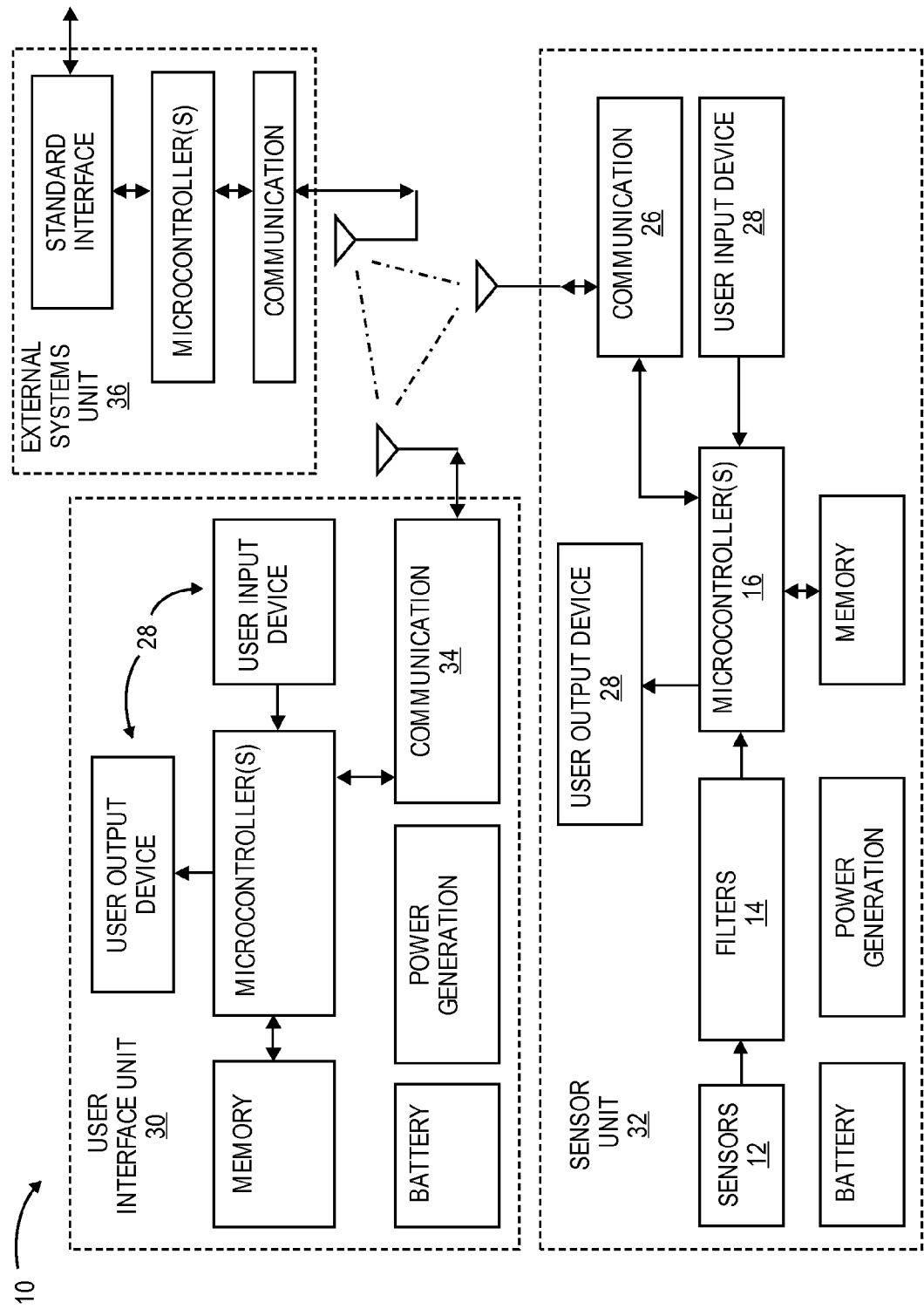
FIG. 5 is a block diagram illustrating an external systems unit in communication with the sensor unit and user interface unit of FIG. 1.

In some embodiments, as shown in FIG. 5, the apparatus 10 may include a communications element 26 to enable the apparatus 10 to communicate with other computing devices, exercise devices, navigation devices, sensors, and any other enabled devices through a communication network, such as the Internet, a local area network, a wide area network, an ad hoc or peer to peer network, combination thereof, and the like. Similarly, the communications element 26 may be configured to allow direct communication between similarly configured apparatuses using USB, Bluetooth, Zigbee, Firewire, and other connections, such that the apparatus 10 need not necessarily utilize a communications network to acquire and exchange information.

In various embodiments the communications element 26 may enable the apparatus 10 to wirelessly communicate with communications networks utilizing wireless data transfer methods such as WiFi (802.11), Wi-Max, Bluetooth, ultra-wideband, infrared, cellular telephony, radio frequency, and the like. However, the communications element 26 may couple with the communications network utilizing wired connections, such as an Ethernet cable, and is not limited to wireless methods.

The communications element 26 may be configured to enable the apparatus 10 to exchange data with external computing devices to facilitate the generation and/or analysis of information. For example, the processing system 16 may use information acquired through the communications element 26 in generating the motion parameter metrics, estimating motion parameters, and correcting statistical models. The processing system 16 may also provide generated motion parameter metrics and estimated motion parameters through the communications element 26 for use by external devices. For instance, the external devices can be configured to store, analyze, and exchange information between a plurality of users and/or a plurality of devices attached to one or multiple users.

Consequently, the communications element 26 generally enables real-time comparison of information generated by the apparatus 10 and other devices. The communications element 26 also enables the apparatus 10 to store data on one or more of the external devices for later retrieval, analysis, aggregation, and the like. The data can be used by individuals, their trainers or others to capture history, evaluate performance, modify training programs, compare against other individuals, and the like. The data can also be used in aggregated form.

The apparatus 10 may additionally include a user interface 28 to enable users to access various information generated and acquired by the apparatus 10, such as acceleration measurements, motion parameter metrics, estimated motion parameters, navigation information acquired from the navigation device 24, information and data acquired through the communications element 26, configuration information, combinations thereof, and the like. The user interface 28 facilities, for example, powering on/off the apparatus 10, selecting which content to display, and providing configuration information such as the attributes of the subject element S.

The user interface 28 may include one or more displays to visually present information for consumption by users and one or more speakers to audibly present information to users. The user interface 28 may also include mechanical elements, such as buzzers and vibrators, to notify users of events through mechanical agitation. In some embodiments, as shown in FIG. 1, the user interface 28 may be implemented within a watch operable to be worn on a user's wrist, forearm, and/or arm. Thus, the user interface 28 may be positioned separately from one or more of the accelerometers 12 to enable the user to easily interact with the apparatus 10. However, in some embodiments the user interface 28 and accelerometers 12 may be integral.

The user interface 28 may also be operable to receive inputs from the user to control the functionality of the processing system 16 and/or devices and elements associated therewith. The user interface 28 may include various functionable inputs such as switches and buttons, a touch-screen display, optical sensors, magnetic sensors, thermal sensors, inertial sensors, a microphone and voice-recognition capabilities, combinations thereof, and the like. The user interface 28 may also include various processing and memory devices to facilitate its functionality.

In some embodiments, the user interface 28 may be able to detect the motion of the user interface unit 30, such as by using accelerations sensed by the one or more accelerometers 12 or additional inertial sensors such as one or more accelerometers associated with the user interface 28, to identify user inputs. For example, the user interface 28 may detect if the user gestures in a particular manner, such as by tapping the user interface unit 30 or other portions of the user interface 28, or by waving his or her hand, and acquire a corresponding user input. Thus, instead of functioning a button or a conventional touch-screen display the user may gesture in a particular manner to control the functionality of the apparatus 10.

In some embodiments, the user interface 28 does not include some or all of the buttons or the like, and the user input normally associated with the buttons is acquired by using inertial sensors and specific motions. For example, the user interface 28 may be operable to acquire user inputs by sensing taps on the user interface 28 and/or user interface unit 30 and estimating the location, direction, strength, count and/or frequency of the taps. For instance, a double tap approximately on the right side of a display associated with the user interface 28 may indicate "select", while a single tap near the top of the display may indicate "scroll up". Consequently, by tapping on the display or other portions of the user interface unit 30, the user may easily provide inputs to the apparatus 10 without functioning buttons or the like. The user interface 28 may also be operable to acquire user inputs based on the orientation of the apparatus 10. For instance, the one or more accelerometers 12 and/or other accelerometers associated with the user interface 28 may be utilized to detect the orientation of the apparatus 10 based on the acceleration and force provided by gravity.

The user interface 28 enables users to receive real-time feedback concerning the estimated motion parameter and associated information. For instance, the user interface 28 may present the currently estimated motion parameter, such as a current stride speed and distance, and/or information associated therewith or with other motion parameters, such as total distance, calories expended, total speed, combinations thereof, and the like.

Figure 10:
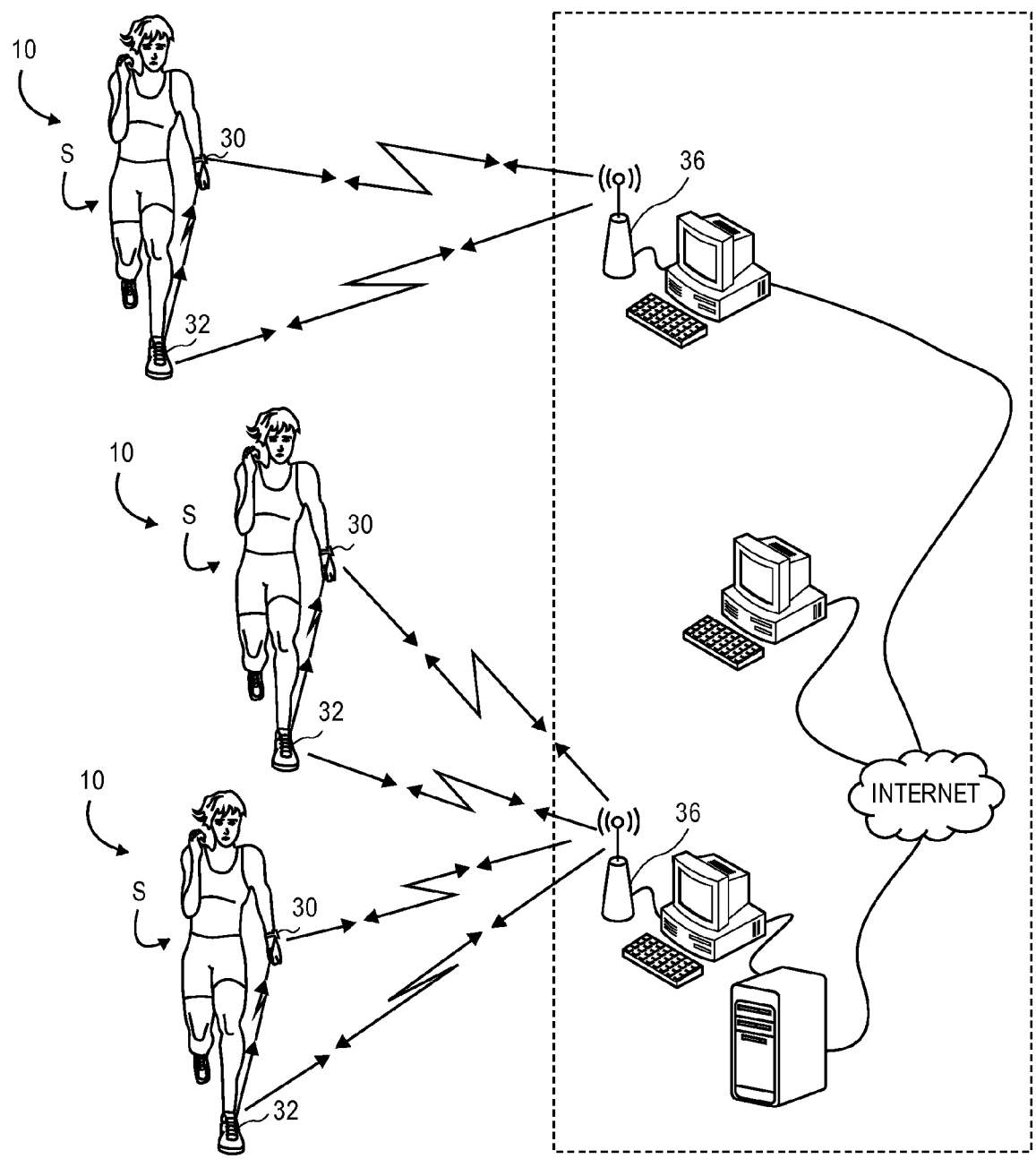
FIG. 10 is a schematic diagram showing the interaction of a plurality of apparatuses configured in accordance with various embodiments of the present invention.

Utilizing the communications element 26, the user interface 28 also enables users to receive real-time feedback and comparisons with other users and devices. For instance, as shown in FIG. 10, a plurality of apparatuses 10 may be employed by a plurality of runners to enable data, metrics, and parameters corresponding to each runner to be shared and presented to the user. Thus, for instance, the user may ascertain the speed and location of other users through the user interface 28.

Further, the user interface 28 may acquire comparison information from the processing system 16 and/or from other devices through the communications element 26 to enable the user to compare his or her performance using the comparison information. For instance, the user interface 28 may present a comparison of the user's current performance with a previous performance by the user, with a training model, and/or with another individual.

In various embodiments, the user may configure the apparatus 10 utilizing the user interface 28 to monitor estimated motion parameters and alert the user through the user interface 28 when one or more estimated motion parameters conflict with a user-defined condition such as an acceptable parameter range, threshold, and/or variance. The user may also configure the apparatus 10 utilizing the user interface 28 to monitor various user-defined goals, such as time limits, motion parameter maximum values, and the like. The apparatus 10 may additionally monitor the estimated motion parameter metrics to determine if the subject element S is in danger and, if necessary, request help using the communications element 26. To facilitate motion parameter monitoring, the user may provide the processing system 16 with various activity programs that may be imported utilizing the communications element 26 or defined through the user interface 28.

Figure 9:
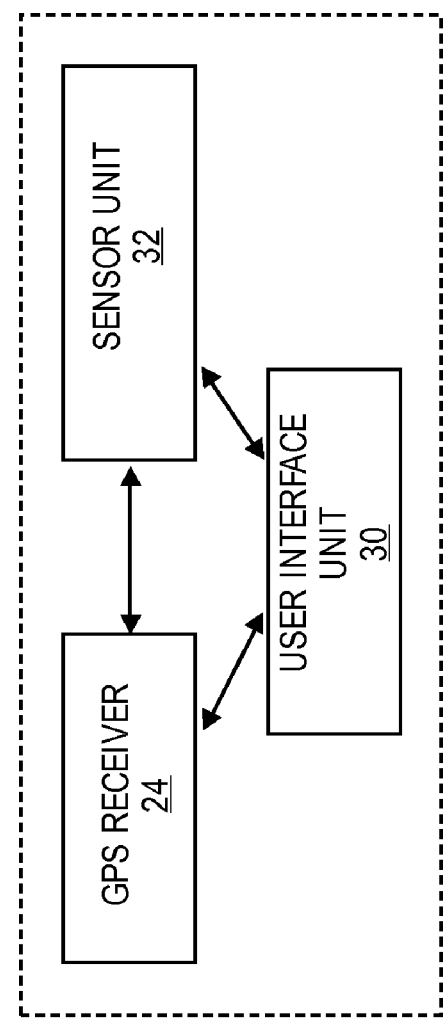
FIG. 9 is a block diagram illustrating another configuration of the GPS receiver, user interface unit, and sensor unit of FIG. 5.

As is discussed above, the various components of the apparatus 10 may be housed integrally or separately in any combination. In some embodiments, the apparatus 10 includes an interface unit 30 for housing the user interface 28 and associated components and a sensor unit 32 for housing the one or more accelerometers 12, the processing system 16, and the communications element 26. In some embodiments, the units 30, 32 may be housed within the same housing, as is shown in FIG. 9. However, in other embodiments the units 30, 32 may be discrete such that the sensor unit 32 may be positioned in a first location, such as on the user's shoe, and the interface unit 30 may be positioned at a second location, such as on the user's wrist.

The interface unit 30 may also include an interface communication element 34, configured in a similar manner to the communications element 26 discussed above, to enable the interface unit 30 to exchange information with the sensor unit 32, other parts of the apparatus 10, and/or with devices external to the apparatus 10. In embodiments where the units 30, 32 are positioned separate from each other, the communications elements 26, 34 may communicate utilizing the various wireless methods discussed above. However, the communications elements 26, 34 may also communicate utilizing wired connections or through external devices and systems.

The units 30, 32 may also each include power sources for powering the various components of the apparatus 10, such as through the use of batteries or power-generating elements such as piezoelectric, electromechanical, thermoelectric, and photoelectric elements. In some embodiments, portions of the user interface 28 may be included with both units 30, 32 such that each unit 30, 32 and its respective components can be individually functioned by the user.

As shown in FIG. 5, the apparatus 10 may additionally include an external systems unit 36 to enable the interface unit 30 and sensor unit 32 to easily communicate with external systems and devices. For example, the external systems unit 36 may include a communications element to communicate with the other communication elements 26, 34, a microcontroller to process information, and a standard interface such as a WiFi, Bluetooth, USB, or ZigBee interface operable to easily interface with devices such as cellular phones, portable media players, personal digital assistants, navigation devices, personal and portable computing devices, combinations thereof, and the like. Thus, in some embodiments, the external systems unit 36 may be connected with an immobile personal computer and the interface unit 30 and sensor unit 32 may be positioned on a mobile user, as is shown in FIG. 10.

Figure 6:
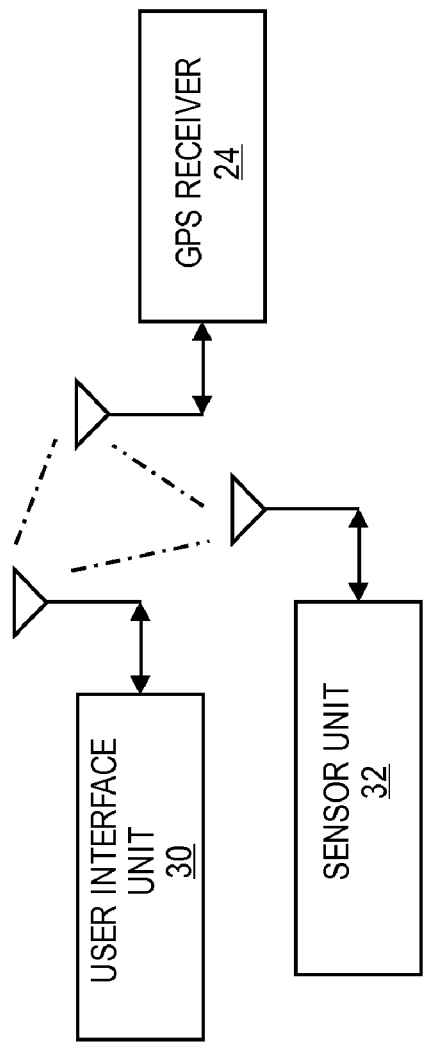
FIG. 6 is a block diagram illustrating the user interface unit and sensor unit of FIG. 5 in communication with a GPS receiver.
Figure 7:
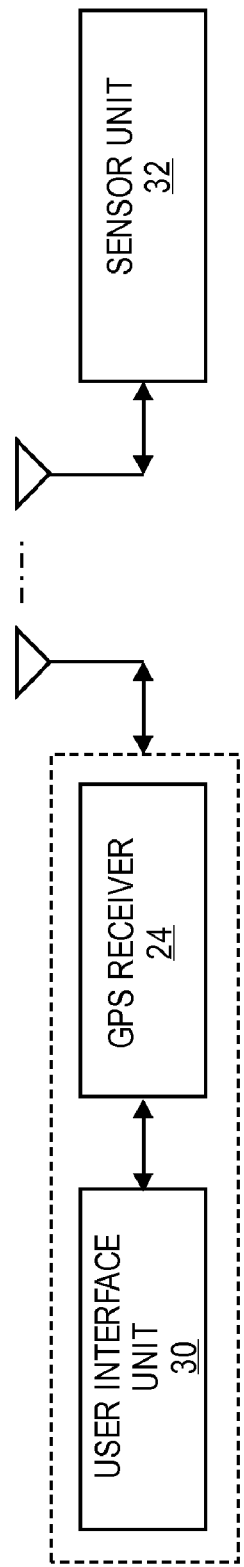
FIG. 7 is a block diagram illustrating another configuration of the user interface unit and GPS receiver of FIG. 5.
Figure 8:
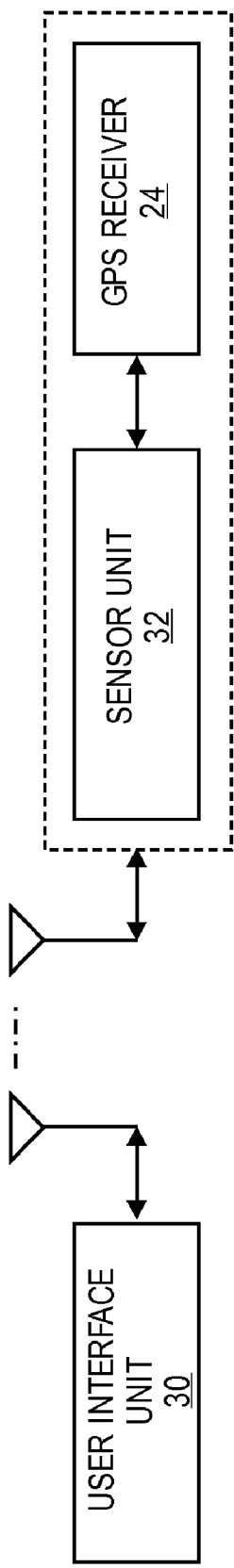
FIG. 8 is a block diagram illustrating another configuration of the sensor unit and GPS receiver of FIG. 5.

As is shown in FIGS. 6 through 9, the interface unit 30 and sensor unit 32 may each be operable to communicate with the navigation unit 24 to receive and utilize navigation information. The navigation device 24 may be discrete from the units 30, 32, as shown in FIG. 6, the navigation device 24 may be integral with the interface unit 30, as shown in FIG. 7, the navigation device 24 may be integral with the sensor unit 32, as shown in FIG. 8, and/or the navigation device 24 may be integral with both units 30, 32, as shown in FIG. 9. Further, in some embodiments, any one or more of the units 30, 32, 36 and navigation device 24 may be automatically disabled when not in use to achieve optimum system power consumption and functionality.

In some embodiments, the sensor unit 32 may be attached to the user's wrist in an enclosure which is similar to a watch and combined with other functionality such as timekeeping or with other sensors such the navigation device 24. In other embodiments, the sensor unit 32 may be attached to the user's arm using an enclosure similar to an armband and combined with other devices such as a cellular phone, an audio device and/or the navigation device 24. In various other embodiments, the sensor unit 32 may be attached to the user with a chest strap in an enclosure which may include other sensors such as a heart-rate monitor (HRM). In yet other embodiments, the sensor unit 32 may be attached to user's waist with, for example, a belt clip. In other embodiments, the sensor unit 32 may be configured to identify its position on the user's body, thereby allowing the user to carry or attach the sensors in an arbitrary location on his or her body such as in a pocket, and/or combined with another device such as a cellular phone.

Consequently, the apparatus 10 is operable to estimate motion parameters using only acceleration measurements acquired from the one or more accelerometers 12, using acceleration measurements in combination with other information acquired from the navigation unit 24 or other devices through the communications element 26, using information other than acceleration measurements, combinations thereof, and the like.

The processing system 16 may additionally monitor the activity of the subject element S utilizing the acceleration measurements, motion parameter metric, and/or estimated motion parameter. In some embodiments, the processing system 16 may utilize acceleration measurements and/or other information to identify the type of activity that the subject element S is engaging in and automatically provide appropriate content based upon the identified activity without requiring user input. For example, if the user switches from walking to jogging, the processing system 16 may identify the change, compute jogging-related metrics and motion parameters, and display jogging-related information using the user interface 28. As another example, the processing system 16 may identify that the user is swimming based upon the acceleration measurements and generate and display swimming-related information such as cadence, stroke power, lap times, and the like.

Other activities which can, for example, be classified or otherwise identified by the processing system 16 include: walking; running; swimming; racquet sports; shuffling; driving; exercising on a stationary bicycle or apparatus; hiking; rollerblading; skateboarding; low-energy activities such as office activities and watching television; sleeping; dancing; playing sports such as basketball, football or golf; combinations thereof; and the like. Thus, the apparatus 10 may automatically provide information for a plurality of activities without requiring manual reconfiguration or programming by the user.

In some embodiments, the processing system 16 may be configured to utilize a multi-resolution approach in storing information and data corresponding to sensed measurements and activities. For example, at the lowest resolution, the time, date, classification, duration and total energy expenditure of each activity may be saved. Another resolution may allow data to be stored corresponding to, for example, for jogging, the average pace, average cadence, total distance, total elevation change, and the like. Another resolution may allow data to be stored corresponding to, again for jogging, for example, individual stride parameters and/or frequent measurements of heart rate, elevation, pace, and/or associated GPS coordinates. The history resolution depth for each type of activity can be pre-selected by the user or be automatically selected by the processing system 16 based on the amount of storage space available. In some embodiments, all activities are initially recorded at the highest available resolution; subsequently, if storage space becomes a constraint, highest resolution records of oldest activities may be erased to allow for storage of the most recent activities at a history resolution at least as good as resolution of the oldest records.

Further, the processing system 16 may provide context-aware functionality utilizing measured accelerations, motion parameter metrics, estimated motion parameters, information acquired through the user interface 28, information acquired through communications element 26 or other devices such as the navigation device 24, combinations thereof, and the like. For example, the processing system 16 may detect: if the apparatus 10 is being used to estimate motion parameters or monitor user performance; if the apparatus 10 is not being used; if the apparatus 10 is being charged; if the apparatus 10 is in proximity to a compatible external system or device; if the apparatus 10 is in proximity to a display device such as a cellular phone, personal digital assistant, computer, audio device, heads-up display, watch; combinations thereof; and the like.

Based on the determination of the use context and with minimal or no user intervention, the apparatus 10 can provide any appropriate set of functions. For example, while in proximity to a compatible external system, the apparatus 10 can automatically establish a communication channel and exchange information with the compatible external system. Similarly, while monitoring user activity, the apparatus 10 can record motion history and associated motion parameters and metrics. While not in use, the apparatus 10 can disable most of its sensors to conserve energy and enable a subset of the sensors, such as the one or more accelerometers 12, only frequently enough to maintain context awareness. While in proximity to a display device, the apparatus 10 can determine the capabilities of the device, and communicate appropriate information to the display device. The use contexts are not necessarily mutually exclusive. For example, the apparatus 10 can be charging and be in proximity to a compatible external system at the same time. Thus, while charging, the apparatus 10 can continue the sensing of nearby compatible external systems and, upon detection of a compatible external system, establish a communication channel and exchange information with the compatible external system. The user thus perceives and expects the apparatus 10 to be always enabled and the apparatus 10 requires minimal or no user input to perform all of its functions.

The activity monitoring and/or context awareness discussed above may be utilized by the apparatus 10 to maintain a generally continuous record of the user's activities. For example, the user may wear the apparatus 10 continuously or repeatedly to monitor long-term activity, such as trends, goals, and the like. Generally continuous monitoring of user activity by the apparatus 10 also enables alerts to be issued if the processing system 16 detects abnormal activity. For example, if the user remains generally immobile for extended periods of time, the processing system 16 may issue an alert to notify the user through the user interface 28 and/or alert third-parties utilizing the communications element 26.

It is believed that embodiments of the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A method of estimating a motion parameter corresponding to a subject element in cyclical motion, the method comprising:
    acquiring an acceleration measurement corresponding to at least one motion cycle;
    determining a stride duration using the acceleration measurement;
    low-pass filtering the acceleration measurement utilizing a cut-off frequency between about 0.5 Hz and 10 Hz;
    calculating an acceleration magnitude using the filtered acceleration measurement;
    for each motion cycle, generating a motion parameter metric utilizing the stride duration and acceleration magnitude; and
    estimating the motion parameter using the motion parameter metric.

2. The method as claimed in claim 1, wherein the motion parameter is estimated utilizing the motion parameter metric and a statistical model.

3. The method as claimed in claim 2, wherein the statistical model is a regression model selected from the group consisting of a linear regression model, a polynomial regression model, a multiple-regression model, a piecewise-linear regression model, and combinations thereof.

4. The method as claimed in claim 1, further including acquiring a plurality of acceleration measurements and generating the motion parameter metric utilizing the acceleration measurements.

5. The method as claimed in claim 1, wherein the cut-off frequency is generated using a stride frequency calculated from the acceleration measurements.

6. The method as claimed in claim 1, wherein the estimated motion parameter is selected from the group consisting of stride speed, acceleration, velocity, stride distance, total distance, gait efficiency, power, energy, maximum impact, average calories consumed, maximum speed change, speed variability, and combinations thereof.

7. The method as claimed in claim 1, wherein the motion parameter corresponds to a stride speed and the motion parameter metric is at least partially generated by performing an integration of a function of the acceleration magnitude.

8. An apparatus operable to estimate a motion parameter corresponding to a subject element, the apparatus comprising:
    a plurality of accelerometers each operable to provide a signal corresponding to an acceleration measurement, at least two of the accelerometers being adapted to measure accelerations in two directions separated by an angle greater than zero degrees; and
    a processing system coupled with one or more of the accelerometers, the processing system operable to:
        calculate a stride duration using at least one of the acceleration measurements,
        low-pass filter the signals corresponding to the acceleration measurements utilizing a cut-off frequency between about 0.5 Hz and 10 Hz,
        calculate an acceleration magnitude using the acceleration measurements corresponding to the filtered signals,
        generate a motion parameter metric utilizing the stride duration and acceleration magnitude, and
        estimate the motion parameter using the motion parameter metric and a statistical regression model.

9. The apparatus as claimed in claim 8, wherein the motion parameter corresponds to a stride speed and the motion parameter metric is at least partially generated by performing an integration of a function of the acceleration magnitude.

10. The apparatus as claimed in claim 8, wherein the apparatus includes at least three accelerometers adapted to measure accelerations in three directions each separated by an angle greater than zero degrees.

11. The apparatus as claimed in claim 8, wherein the processing system is further operable to limit acceleration measurements to within a specific dynamic range.

* * * * *